United States Patent [19]
MacDonald et al.

[11] Patent Number: 6,117,898
[45] Date of Patent: Sep. 12, 2000

[54] BICYCLIC AMIDINE DERIVATIVES AS INHIBITORS OF NITRIC OXIDE SYNTHETASE

[75] Inventors: James Edwin MacDonald, Pittsford; William Calvin Shakespeare, Rochester; Robert John Murray, Brighton; James Russell Matz, Fairport, all of N.Y.

[73] Assignee: Astra Aktiebolag, Sodertalje, Sweden

[21] Appl. No.: 09/358,427

[22] Filed: Jul. 22, 1999

Related U.S. Application Data

[62] Continuation of application No. 09/111,483, Jul. 8, 1998, abandoned, which is a division of application No. 08/737, 286, filed as application No. PCT/GB95/01041, May 9, 1995, Pat. No. 5,807,886.

[30] Foreign Application Priority Data

May 7, 1994 [GB] United Kingdom .................. 9409201
May 12, 1994 [GB] United Kingdom .................. 9409462

[51] Int. Cl.[7] .......................... A61K 31/38; A61K 31/34; A61K 31/55; A61K 31/47
[52] U.S. Cl. ..................... 514/438; 514/471; 514/213; 514/310
[58] Field of Search .................. 514/438, 471, 514/213, 310

[56] References Cited

U.S. PATENT DOCUMENTS

| | | | |
|---|---|---|---|
| 3,632,593 | 1/1972 | Gutier et al. ............... | 260/296 |
| 3,669,974 | 6/1972 | Elpern et al. .............. | 546/231 |
| 3,993,469 | 11/1976 | Regal et al. ................ | 71/92 |
| 4,073,639 | 2/1978 | Regel et al. ................ | 71/92 |

FOREIGN PATENT DOCUMENTS

| | | |
|---|---|---|
| 717 740 | 1/1969 | Belgium . |
| 0 446 699 | 9/1991 | European Pat. Off. . |
| 0 547 558 | 6/1993 | European Pat. Off. . |
| 0 558 468 | 9/1993 | European Pat. Off. . |
| 0 676 196 | 4/1995 | European Pat. Off. . |
| 2 321 330 | 11/1974 | Germany . |
| 1 088 095 | 10/1964 | United Kingdom . |
| 2 226 562 | 2/1970 | United Kingdom . |
| 1 180 629 | 7/1990 | United Kingdom . |
| 9 204 054 | 8/1990 | WIPO . |
| 9 324 126 | 3/1992 | WIPO . |
| 9 313 055 | 7/1993 | WIPO . |
| 9 412 163 | 6/1994 | WIPO . |
| 9 412 165 | 6/1994 | WIPO . |
| 9 421 621 | 9/1994 | WIPO . |
| 9 500 505 | 1/1995 | WIPO . |
| 9 505 363 | 2/1995 | WIPO . |
| 9 509 619 | 4/1995 | WIPO . |
| 9 509 621 | 4/1995 | WIPO . |
| 9 510 266 | 4/1995 | WIPO . |
| 9 511 014 | 4/1995 | WIPO . |
| 9 511 231 | 4/1995 | WIPO . |

OTHER PUBLICATIONS

Moncada et al, "Nitric oxide; Physiology, . . . " Pharmacological Reviews, vol. 43, pp. 109–142 (1991).
Nissan Chem. Ind. KK (1989) "Fluorine–contg cpds." (0–38310/42).
Forstermann et al, "Induced RAW 264.7 macrophages express," European J. of Pharmacology–Molec. Pharmac. Sect. vol. 225, pp. 161–165 (1992).
Bredt et al, "Isolation of nitric oxide synthetase . . . ," Proc. Natl. Acad. Sci. (USA), vol. 87, pp. 682–685 (1990).
Pollock et al, "Purification and characterization of . . . ," Proc. Natl. Acad. Sci. (USA), vol. 88, pp. 10480–10484 (1991).

*Primary Examiner*—Deborah C. Lambkin
*Attorney, Agent, or Firm*—Nixon & Vanderhye

[57] ABSTRACT

There are provided compounds of formula (I),

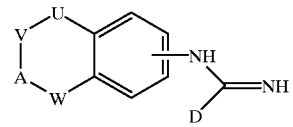

wherein D represents a five membered heterocyclic aromatic ring containing 1 to 4 heteroatoms selected from O, N or S, optionally substituted at a carbon atom by halogen, trifluoromethyl, alkyl C1 to 6, nitro or cyano, and which is connected to the remainder of the compound of formula (I) through a carbon atom; A represents N(X) or CH(—(CH$_2$)$_m$—NXY); U represents NH, O or CH$_2$; V represents (CH$_2$)$_a$; W represents (CH$_2$)$_b$; a, b, m, X and Y are as defined in the specification, together with processes for their preparation and compositions containing them. Compounds of formula (I) are nitric oxide synthetase inhibitors and are useful in therapy.

16 Claims, No Drawings

BICYCLIC AMIDINE DERIVATIVES AS INHIBITORS OF NITRIC OXIDE SYNTHETASE

This application is a continuation of U.S. Ser. No. 09/111,483 Jul. 8, 1998 abandoned, which is a divisional of U.S. Ser. No. 08/737,286 Nov. 5, 1996, U.S. Pat. No. 5,807,886, which is a 371 of PCT/GB95/01041 May 9, 1995.

This invention relates to bicyclic amidine derivatives, process for their preparation, compositions containing them and their use in therapy.

Certain amidine derivatives have been described for use in therapeutic applications. N-Phenyl amidine derivatives have been described for use in the treatment of diabetes in U.S. Pat. No. 3,669,974 (USV Pharmaceutical Corp.) and UK Patent Application 2226562 (Boots). N'N"disubstituted amidines are described for use in the treatment of hypertension, depression and hallucinogenic states in International Patent Application WO 92/04054 (University of Oregon). The use of certain amidines and symmetric bisamidines as analgesics, in the treatment of inflammation and in the treatment of hypertension is described in Belgian Patent No. 717740 and UK Patent No. 1180629 (both of Delalande). Amidine derivatives have also been described for use as herbicides in German Patent Application DE-OS-2321330 (Bayer).

The use of inhibitors of nitric oxide synthetase in the treatment of disease has also been described, for example, in International Patent Applications WO 94/12163 (Abbott), WO 93/13066 and WO 94/12165 (both of Wellcome) and European Patent Applications 446699 (Merrell Dow), 547558 and 558468 (both of Washington University). The use of nitric oxide synthetase inhibitors in therapy is also described in WO 95/00505, WO 95/09619, WO 95/09621 (all of Wellcome), WO 95/10266 (Otsuka), WO 95/11231 and WO 95/11014 (both of Searle) which six documents were published after the earliest priority date of this application.

The applicant has previously described the use of guanidine derivatives and amidine derivatives which are inhibitors of nitric oxide synthetase in the treatment inter alia of neurodegenerative disease (WO 94/21621, WO 95/05363). The second of these was published after the earliest priority date of this application.

We have now found a new group of bicyclic amidine derivatives that possesses useful pharmaceutical activity.

According to a first aspect of the invention, we provide a compound of formula I

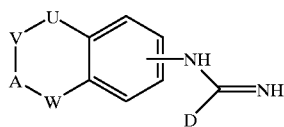

wherein

D represents a five membered heterocyclic aromatic ring containing 1 to 4 heteroatoms selected from O, N or S, optionally substituted at a carbon atom by halogen, trifluoromethyl, alkyl C1 to 6, nitro or cyano, and which is connected to the remainder of the compound of formula I through a carbon atom;

A represents N(X) or CH(—$(CH_2)_m$—NXY);

U represents NH, O or $CH_2$;

V represents $(CH_2)_a$;

W represents $(CH_2)_b$;

a and b independently represent an integer 0 to 3, provided that a+b is in the range 1 to 3;

X and Y independently represent hydrogen, alkyl C1 to 6, or the group —$(CH_2)_nQ$, or —NXY represents piperidinyl, pyrrolidinyl morpholinyl or tetrahydroisoquinolinyl;

Q represents biphenyl or phenyl optionally substituted by one or more groups selected from alkyl C1 to 6, alkoxy C1 to 6, perfluoroalkyl C1 to 6, halogen, nitro or cyano;

m represents an integer 0 to 5;

n represents an integer 0 to 6;

or the chain U—V—A—W is as defined above save that it may be unsaturated, or the chain U—V—A—W may represent —NH—$CH_2$—$CH_2$—O— substituted at a carbon atom by the group —$(CH_2)_m$—NXY, wherein m, X and Y are as defined above, and pharmaceutically acceptable salts thereof.

A preferred group of compounds of formula I is defined by formula IA:

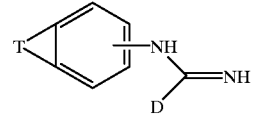

wherein

T represents a $C_{3-5}$ saturated or unsaturated alkylene chain substituted by —$(CH_2)_m$—NXY; —O—$(CH_2)_2$—NH— substituted by —$(CH_2)_m$—NXY; or —U—$(CH_2)_a$—N(X)—$(CH_2)_b$—;

X and Y independently represent hydrogen, alkyl C1 to 6, or the group —$(CH_2)_nQ$, or —NXY represents piperidinyl, pyrrolidinyl, morpholinyl or tetrahydroisoquinolinyl;

Q represents phenyl optionally substituted by alkyl C1 to 6, alkoxy C1 to 6, trifluoromethyl, halogen, nitro or cyano;

and U, m, n, a, b and D are as defined above, save that when T represents —U—$(CH_2)_a$—N(X)—$(CH_2)_b$— and X represents —$(CH_2)_nQ$, n represents an integer 0 to 5, and pharmaceutically acceptable salts thereof.

We prefer that D represents a five-membered heterocyclic aromatic ring containing one heteroatom selected from O, N or S, optionally substituted at a carbon atom by halogen. We particularly prefer that D represents thienyl, furyl or pyrrolyl, especially thienyl or furyl, more especially thienyl and most especially 2-thienyl.

We prefer that T represents a $C_{3-5}$ saturated or unsaturated alkylene chain substituted by —$(CH_2)_m$—NXY, particularly a $C_{3-5}$ saturated alkylene chain substituted by —$(CH_2)_m$—NXY, especially a $C_{3-4}$ saturated alkylene chain substituted by —$(CH_2)_m$—NXY.

When T represents a $C_{3-5}$ saturated or unsaturated alkylene chain substituted by —$(CH_2)_m$—NXY; or —O—$(CH_2)_2$—NH— substituted by —$(CH_2)_m$—NXY, we prefer that X and Y independently represent hydrogen, alkyl C1 to 6 or the group —$(CH_2)_nQ$. We particularly prefer that X and Y independently represent hydrogen, methyl, ethyl or the group —$(CH_2)_nQ$ and especially that one of X and Y represents hydrogen and the other represents hydrogen or the group —$(CH_2)_nQ$.

We prefer that m represents 0 or 1, especially 0.

When T represents —U—(CH$_2$)$_a$—N(X)—(CH$_2$)$_b$—, we prefer U to represent CH$_2$.

When T represents —U—(CH$_2$)$_a$—N(X)—(CH$_2$)$_b$—, we prefer that a+b is 1 or 2.

When T represents —U—(CH$_2$)$_a$—N(X)—(CH$_2$)$_b$—, we prefer that X represents hydrogen, alkyl C1 to 6 or the group —(CH$_2$)$_a$Q.

When X and/or Y represent —(CH$_2$)$_n$Q, we prefer that n represents 0, 1 or 2, especially 1.

We prefer that Q represents phenyl optionally substituted by alkyl C1 to 6 or halogen, although we particularly prefer that Q represents unsubstituted phenyl.

According to the invention, we further provide a process for the preparation of compounds of formula I, and pharmaceutically acceptable salts thereof which comprises:

(a) preparing a compound of formula I by reacting a corresponding compound of formula II

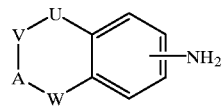

II wherein U, V, A and W are as defined above, with a compound of formula III

III wherein D is as defined above and L is a leaving group;

(b) preparing a compound of formula I by reacting a corresponding compound of formula IV

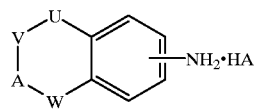

IV wherein U, V, A and W are as defined above and HA is an acid, with a compound of formula V

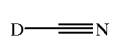

V wherein D is as defined above;

(c) preparing a compound of formula I in which A represents N(X) and X represents alkyl C1 to 6 or the group —(CH$_2$)$_a$Q by reacting a corresponding compound of formula I in which X represents hydrogen with a compound of formula VI

VI wherein R$^9$ represents alkyl C1 to 6 or the group —(CH$_2$)$_a$Q and L is a leaving group;

(d) preparing a compound of formula I in which A represents CH(—(CH$_2$)$_m$—NXY) and at least one of X and Y represents alkyl C1 to 6 or the group —(CH$_2$)$_a$Q by reacting a corresponding compound of formula I in which one or both of X and Y represents hydrogen with a compound of formula VI;

(e) preparing a compound of formula I in which A represents CH(—(CH$_2$)$_m$—NXY) and m represents an integer 1 to 5, by reduction of a corresponding compound of formula VII

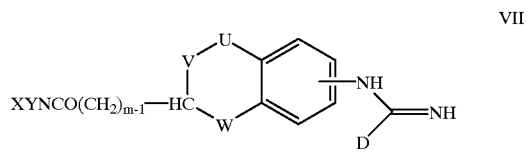

VII wherein U, V, W, X, Y and D are as defined above;

(f) preparing of a compound of formula I in which A represents CH(—CH$_2$)$_m$—NXY) and both X and Y represent hydrogen, by reduction of a corresponding compound of formula VIII

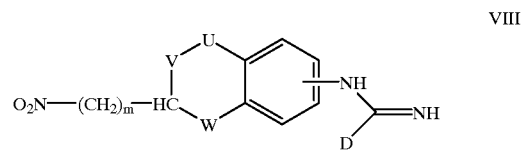

VIII wherein U, V, W, m and D are as defined above;

(g) preparing a compound of formula I in which A represents CH(—(CH$_2$)$_m$—NXY), X represents hydrogen and m represents an integer 1 to 5, by reduction of a corresponding compound of formula IX

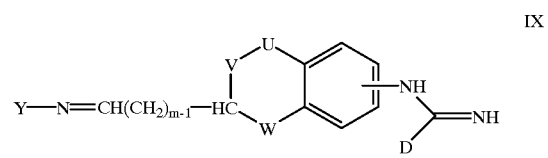

IX wherein U, V, W, D and Y are as defined above;

(h) preparing a compound of formula I wherein A represents CH(—(CH$_2$)$_m$—NXY), one of X and Y represents hydrogen, and the other represents —(CH$_2$)$_n$Q in which n represents an integer 1 to 6, by reduction of a corresponding compound of formula X

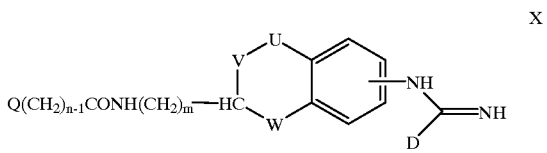

X wherein Q, m, U, V, W and D are as defined above;

(i) preparing a compound of formula I wherein A represents CH(—(CH$_2$)$_m$—NXY), one of X and Y represents hydrogen, and the other represents —(CH$_2$)$_n$Q in which n represents an integer 1 to 6, by reduction of a compound of formula XI

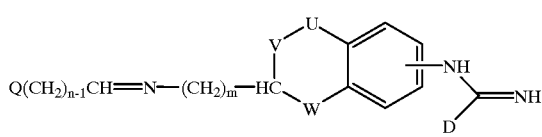

wherein Q, m, U, V, W and D are as defined above; or (j) preparing a compound of formula I in which A represents CH(—NXY) and X represents hydrogen by reduction of a corresponding compound of formula XII

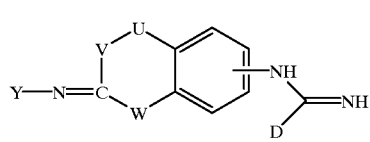

wherein U, V, W, D and Y are as defined above;

and where desired or necessary converting the resultant compound of formula I, or another salt thereof, to a pharmaceutically acceptable salt thereof, or vice versa.

In process (a), the reaction will take place on stirring a mixture of the reactants in a suitable solvent, for example a lower alkanol e.g. ethanol isopropanol or tertiary butanol, at a temperature between room temperature and the reflux temperature of the solvent. The reaction time will depend inter alia on the solvent and the nature of the leaving group, and may be up to 48 hours, however it will typically be from 1 to 5 hours. Suitable leaving groups that L may represent include thioalkyl, sulphonyl, trifluorocarbon sulphonyl halide, alkyl and aryl alcohols and tosyl groups; others are recited in 'Advanced Organic Chemistry', J. March (1985) 3rd Edition, McGraw-Hill on page 315 and are well known in the art.

In process (b), the reaction is preferably performed by refluxing a mixture of the two compounds for several hours in the presence of a suitable solvent whereby the reaction temperature is high enough so that condensation takes place readily, but not sufficiently high to decompose the amidine formed. The reaction temperature can vary from room temperature to about 250° C., although it is preferable to perform the reaction at temperatures from about 100° C. to 200° C. We find that o-dichlorobenzene is a particularly suitable solvent and it is useful to add 4-dimethylaminopyridine as a catalyst. On cooling, two layers form, the solvent may be decanted, and the reaction worked up by addition of aqueous base. Alternatively, where the reactants are soluble in the solvent, the solvent may be evaporated off under vacuum and the reaction mixture worked up by addition of water. The acid HA may be an organic or inorganic acid, for instance, hydrochloric, hydrobromic, hydroiodic, sulphuric, nitric, phosphoric, acetic, lactic, succinic, fumaric, malic, maleic, tartaric, citric, benzoic or methanesulphonic acid.

In process (c), the reaction will take place under standard conditions, for example by reacting the two compounds in an inert solvent under basic conditions at room temperature for a period of up to 12 hours. We have frequently found it desirable to treat the amine with NaH before reacting with the compound of formula VI. We prefer that L represents halide, particularly bromide.

Process (d) may be performed under conditions analogous to those described above for process (c).

In process (e), the reduction may be performed by treatment with diborane in an inert solvent e.g. THF. Alternative although less preferred reagents which may be suitable include lithium aluminium hydride and reagents for catalytic hydrogenation e.g. $H_2$ on Pd/C. Further details of the reaction conditions for use of these reactions may be obtained by reference to J. March "Advanced Organic Chemistry" on page 1099, including the references cited therein.

In process (f), the reduction reaction may be performed under a number of conditions, for example those described in J March "Advanced Organic Chemistry" on pages 1103–1104. These include catalytic hydrogenation, use of Zn, Sn or Fe metal, $AlH_3$—$AlCl_3$, sulphides and others. We prefer to perform the reaction by hydrogenation at atmospheric pressure for 3–6 hours in the presence of a palladium and carbon catalyst.

In processes (g), (i) and (j), the reduction may be performed by treating the compound with sodium borohydride or sodium cyanoborohydride under standard conditions.

In process (h) the reaction may be performed under conditions analogous to those described above for process (e).

Salts of compounds of formula I may be formed by reacting the free base or a salt, enantiomer, tautomer or protected derivative thereof, with one or more equivalents of the appropriate acid. The reaction may be carried out in a solvent or medium in which the salt is insoluble or in a solvent in which the salt is soluble, eg water, dioxan, ethanol, tetrahydrofuran or diethyl ether, or a mixture of solvents, which may be removed in vacuo or by freeze drying. The reaction may be a metathetical process or it may be carried out on an ion exchange resin.

The compounds of formula II may be prepared by reduction of a corresponding compound of formula XIII

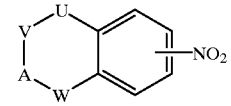

wherein U, V, A and W are as defined above.

The reduction reaction may be performed under analogous conditions to those described above for process (f).

Certain compounds of formula II are either known or may be prepared by conventional methods known per se. Other compounds of formula II may be prepared from known compounds with simpler substituent groups by following analogous processes to those described above for processes (c) to (j). For example, by analogy with process (j) above, we find it convenient to prepare certain compounds of formula XIII in which A represents CH(—NXY) and X represents hydrogen by reduction of the corresponding imine formed by reaction of a compound of formula $NH_2Y$ with the nitrated bicyclic ketone.

Compounds of formula IV may be prepared by analogous processes to those described for the preparation of compounds of formula II. Compounds of formula IV may be converted to corresponding compounds of formula II by treatment with a base. Compounds of formula II may be converted to corresponding compounds of formula IV by treatment with a protic acid HA, for example one of those listed above.

Compounds of formula III are either known or may be prepared by known methods. For example, compounds of formula III in which L represents thioalkyl may be prepared by treatment of the corresponding thiamide of formula XIV

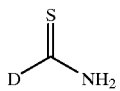

XIV wherein D is as defined above,
with an alkyliodide.

Compounds of formula VII, VIII, IX, X, XI and XII may be prepared by analogous processes to those described for the preparation of compounds of formula I. Such compounds may be readily prepared from compounds with simpler substituent groups by conventional methods e.g. formation of an amide (VII, X) by reaction of an amine with a carboxylic acid or activated derivative thereof or formation of an imine (IX, XI, XII) by reaction of an amine with an aldehyde.

Compounds of formula V, VI, XII and XIV are either known or may be prepared by conventional methods known per se.

It will be apparent to a person skilled in the art that it may be desirable to protect an amine or other reactive group using a protecting group as described in the standard text "Protecting groups in Organic Synthesis", 2nd Edition (1991) by Greene and Wuts. Amine-protecting groups which may be mentioned include alkyloxycarbonyl C2 to 7, eg t-butyloxycarbonyl, phenylalkyloxycarbonyl C8 to 13, eg benzyloxycarbonyl or preferably trifluoroacetate. Deprotection will normally take place on treatment with aqueous base, acid or by treatment with hydrogen.

The compounds of the invention and intermediates may be isolated from their reaction mixtures by standard techniques.

The term "alkyl C1 to 6" includes straight chain, branched, saturated, unsaturated, aliphatic and cyclic alkyl groups containing 1 to 6 carbon atoms.

The compounds of formula I may exist in tautomeric, enantiomeric or diasteriomeric forms, all of which are included within the scope of the invention. The various optical isomers may be isolated by separation of a racemic mixture of the compounds using conventional techniques, e.g. fractional crystallisation, or HPLC. Alternatively the individual enantiomers may be made by reaction of the appropriate optically active starting materials under reaction conditions which will not cause racemisation.

Intermediate compounds may also exist in enantiomeric forms and may be used as purified enantiomers, diastereomers, racemates or mixtures.

The compounds of formula I possess useful pharmacological activity in animals. In particular, they possess useful nitric oxide synthetase inhibiting activity, and are expected to be useful in the treatment or prophylaxis of human diseases or conditions in which the synthesis or oversynthesis of nitric oxide forms a contributory part; for example, hypoxia, e.g. in cases of cardiac arrest and stroke, neurodegenerative disorders including nerve degeneration and/or nerve necrosis in disorders such as hypoxia, hypoglycemia, epilepsy, and in external wounds (such as spinal cord and head injury), hyperbaric oxygen convulsions and toxicity, dementia e.g. pre-senile dementia, Alzheimer's disease and AIDS-related dementia, Sydenham's chorea, Parkinson's disease, Tourette's Syndrome, Huntington's disease, Amyotrophic Lateral Sclerosis, Korsakoff's disease, imbecility relating to a cerebral vessel disorder, sleeping disorders, schizophrenia, depression, autism, seasonal affective disorder, jet-lag, depression or other symptoms associated with Premenstrual Syndrome (PMS), anxiety and septic shock. Compounds of formula I may also be expected to show activity in the prevention and reversal of tolerance to opiates and diazepines, treatment of drug addiction, relief of pain and treatment of migraine and other vascular headaches. The compounds of the present invention may also show useful immunosuppressive activity, be useful in the treatment or prophylaxis of inflammation, neurogenic inflammation, reversible obstructive airways disease including asthma and adult respiratory distress syndrome (ARDS), in the treatment of gastrointestinal motility disorders, cancer, in the induction of labour, for reduction of gastric acid secretion and for increasing the contractile force of skeletal muscle.

Compounds of formula I are most particularly of interest in the treatment of neurodegenerative disorders, of migraine or for the prevention and reversal of tolerance to opiates and diazepines or for the treatment of drug addiction and especially in the treatment of neurodegenerative disorder Thus according to a further aspect of the invention we provide a compound of formula I, or a pharmaceutically acceptable salt thereof, for use as a pharmaceutical.

According to another feature of the invention we provide the use of a compound of formula I, or a pharmaceutically acceptable salt thereof, in the manufacture of a medicament for the treatment or prophylaxis of the aforementioned diseases or conditions.

There is also provided a method of treatment or prophylaxis of one of the aforementioned diseases or conditions which comprises administering a therapeutically effective amount of a compound of formula I or a pharmaceutically acceptable salt thereof, to a person suffering from or susceptible to such a disease or condition.

For the above mentioned therapeutic indications, the dosage administered will, of course, vary with the compound employed, the mode of administration and the treatment desired. However, in general satisfactory results are obtained when the compounds are administered to a human at a daily dosage of between 1 mg and 2000 mg (measured as the solid form).

The compounds of formula I, and pharmaceutically acceptable salts thereof, may be used on their own, or in the form of appropriate medicinal preparations for enteral or parenteral administration.

According to the invention, there is provided a pharmaceutical formulation including preferably less than 80% and more preferably less than 50% of a compound of formula I, or a pharmaceutically acceptable salt thereof, in admixture with a pharmaceutically acceptable diluent or carrier.

Examples of diluents and carriers which are suitable will be well known to a person skilled in the art.

The enzyme nitric oxide synthetase has a number of isoforms and compounds of formula I, or pharmaceutically acceptable salts thereof, may be screened for nitric oxide synthetase activity by procedures based on those of Bredt and Snyder in Proc. Natl. Acad. Sci. (1990) 87, 682–685 and Förstermann et. al., Eur. J. Pharm. (1992) 225, 161–165 as follows. Nitric oxide synthetase converts $^3$H-L-arginine to $^1$H-L-citrulline which can be separated by cation exchange chromatography and quantified by scintillation counting.

Screen A (A) Screen for Neuronal Nitric Oxide Synthetase Activity

Enzyme was isolated from rat hippocampus or cerebellum. The cerebellum or hippocampus of a male Sprague-Dawley rat (250–275 g) is removed following $CO_2$ anaesthesia of the animal and decapitation. Cerebellar or hippocampal supernatant is prepared by homogenisation in 50 mM Tris-HCl with 1 mM EDTA buffer (pH 7.2 at 25° C.) and centifugation for 15 minutes at 20.000 g. Residual L-arginine is removed from the supernatant by chromatography through Dowex AG-50W-X8 sodium form and hydrogen form columns successively, and further centrifugation at 1000 g for 30 seconds.

For the assay, 25 μl of the final supernatant is added to each of 12 test tubes containing 25 μl L-arginine solution (of concentration 18 μM $^1$H-L-arginine, 96 nM $^3$H-L-arginine) and either 25 μl of an assay buffer (50 mM HEPES, 1 mM EDTA, 1.5 mM CaCl$_2$, pH 7.4) or 25 μl of test compound in the buffer at 2220 C. To each test tube is added 75 μl of complete assay buffer (50 mM HEPES, 1 mM EDTA, 1.5 mM CaCl$_2$, 1 mM DTT, 100 μM NADPH, 10 μg/ml calmodulin, pH 7.4) to initiate the reaction and the reaction is stopped after 10 minutes by addition of 2 ml of a termination buffer (20 mM HEPES, 2 mM EDTA, pH 5.5).

Labelled L-citrulline is separated from labelled L-arginine by chromatography over a Dowex AG-50W-X8 200–400 mesh column. 1 ml of each terminated reaction is added to an individual 1 ml column and the eluant combined with that from two 1 ml distilled water washes and 16 ml of scintillation cocktail. The L-citrulline is then quantified by scintillation counting.

In a typical experiment using the cerebellar supernatant, basal activity is increased by 20,000 dpm/ml of sample above a reagent blank which has an activity of 7,000 dpm/ml. A reference standard, N-nitro-L-arginine, which gives 60% inhibition of nitric oxide synthetase at a concentration of 1 μM, is tested in the assay to verify the procedure.

Screen B (B) Screen for Macrophage Nitric Oxide Synthetase Activity

Enzyme is prepared, after induction, from the cultured murine macrophage cell line J774A-1 (obtained from laboratories of the Imperial Cancer Research Fund). J774A-1 cells are cultured in Dulbecco's Modified Eagles Medium (DMEM) supplemented with 10% foetal bovine serum, 4 mM L-glutamine and antibiotics (100 units/ml penicillin G, 100 μg/ml streptomycin & 0.25 μg/ml amphotericin B). Cells are routinely grown in 225 cm$^2$ flasks containing 35 ml medium kept at 37° C. and in a humidified atmosphere containing 5% CO$_2$.

Nitric oxide synthetase is produced by cells in response to interferon-γ (IFN-γ) and lipopolysaccharide (LPS). The medium from confluent culture flasks is removed and replaced with 25 ml (per flask) of fresh medium containing 1 μg/ml LPS and 10 units/ml IFN-γ. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 μM dithiothreitol and a cocktail of protease inhibitors comprising leupeptin (2 μg/ml), soya bean trypsin inhibitor (10 μg/ml), aprotinin (5 μg/ml) & phenylmethylsulphonyl fluoride (50 μg/ml).

For the assay, 25 μl substrate cocktail (50 mM Tris-HCl (pH 7.5 at 20° C.), 400 μM NADPH, 20 μM flavin adenine dinucleotide, 20 μM flavin mononucleotide, 4 μM tetrahydrobiopterin, 12 μM L-arginine and 0.025 μCi L-[$^3$H] arginine) is added to wells of a 96 well filter plate (0.45 μM pore size) containing 25 μl of a solution of test compound in 50 mM Tris-HCl. The reaction is started by adding 50 μl of cell lysate (prepared as above) and after incubation for 1 hour at room temperature is terminated by addition of 50 μl of an aqueous solution of 3 mM nitroarginine and 21 mM EDTA.

Labelled L-citrulline is separated from labelled L-arginine using Dowex AG-50W. 150 μl of a 25% aqueous slurry of Dowex 50W (Na$^+$ form) is added to the assay after which the whole is filtered into 96 well plates. 70 μl of filtrate is sampled and added to wells of 96 well plates containing solid scintillant. After allowing the samples to dry the L-citrulline is quantified by scintillation counting.

In a typical experiment basal activity is 300 dpm per 70 μl sample which is increased to 1900 dpm in the reagent controls. Aminoguanidine, which gives an IC$_{50}$ (50% inhibitory concentration) of 10 μM, is tested as a standard to verify the procedure.

Screen C (C) Screen for Endothelial Nitric Oxide Synthetase Activity

Enzyme may be isolated from human umbilical vein endothelial cells (HUVECs) by a procedure based on that of Pollock et al (1991) Proc. Nat. Acad. Sci., 88, 10480–10484. HUVECs were purchased from Clonetics Corp (San Diego, Calif., USA) and cultured to confluency. Cells can be maintained to passage 35–40 without significant loss of yield of nitric oxide synthetase. When cells reach confluency, they are resuspended in Dulbecco's phosphate buffered saline, centrifuged at 800 rpm for 10 mins, the cell pellet homogenised in ice-cold 50 mM Tris-HCl, 1 mM EDTA, 10% glycerol, 1 mM phenylmethylsulphonylfluoride, 2 μM leupeptin at pH 4.2. Following centrifugation at 34,000 rpm for 60 mins, the pellet is solubtlised in the homogenisation buffer which also contains 20 mM CHAPS. After a 30 min incubation on ice, the suspension is centrifuged at 34,000 rpm for 30 mins. The resulting supernatant is stored at −80° C. until use.

For the assay, 25 μl of the final supernatant is added to each of 12 test tubes containing 25 μl L-arginine solution (of concentration 12 μM $^1$H-L-arginine, 64 nM $^3$H-L-arginine) and either 25 μl of an assay buffer (50 mM HEPES, 1 mM EDTA, 1.5 mM CaCl$_2$, pH 7.4) or 25 μl of test compound in the buffer at 22° C. To each test tube was added 25 μl of complete assay buffer (50 mM HEPES, 1 mM EDTA, 1.5 mM CaCl$_2$, 1 mM DTT, 100 μM NADPH, 10 μg/ml calmodulin, 12 μM tetrahydrobiopterin, pH 7.4) to initiate the reaction and the reaction is stopped after 10 mins by addition of 2 ml of a termination buffer (20 mM HEPES, 2 mM EDTA, pH 55).

Labelled L-citrulline is separated from labelled L-arginine by chromatography over a Dowex AG-50W-X8 200–400 mesh column. 1 ml of each terminated reaction is added to an individual 1 ml column and the eluant combined with that from two 1 ml distilled water washes and 16 ml of scintillation cocktail. The L-citrulline is then quantified by scintillation counting.

In a typical experiment, basal activity is increased by 5,000 dpm/ml of sample above a reagent blank which has an activity of 1500 dpm/ml. A reference standard, N-nitro-L-arginine, which gives 70–90% inhibition of nitric oxide synthetase at a concentration of 1 μM, is tested in the assay to verify the procedure.

Compounds may also be tested in an ex-vivo assay to determine the extent of brain penetration.

Screen D (D) Ex vivo Assay for Neuronal Nitric Oxide Synthetase Activity

Male Sprague-Dawley rats (250–275 g) were dosed intravenously at 10 mg/kg with test compound dissolved in 0.9% saline or with saline alone as control. At a predetermined time (typically 2–24 hours) after treatment, the animals were sacrificed, the cerebellum removed and the supernatant prepared and assayed for nitric oxide synthetase activity as described in Screen A.

As a further confirmatory test, a fraction of the cerebellar supernatant was applied to a 2'–5'-ADP Sepharose column (which binds nitric oxide synthetase) and subsequently eluted with NADPH. The eluant was tested for nitric oxide synthetase activity following the procedure of Screen A.

Compounds that penetrate the rat brain and inhibit neuronal nitric oxide synthetase resulted in reduced nitric oxide synthetase activity both in the supernatant preparation and in the eluant from the 2'–5'-ADP Sepharose column.

In the screens for nitric oxide synthetase inhibition activity, compound activity is expressed as $IC_{50}$ (the concentration of drug substance which gives 50% enzyme inhibition in the assay). $IC_{50}$ values for test compounds were initially estimated from the inhibiting activity of 1, 10 and 100 $\mu$M solutions of the compounds. Compounds that inhibited the enzyme by at least 50% at 10 $\mu$M were retested using more appropriate concentrations so that an $IC_{50}$ could be determined.

In Screen A above (a screen for activity against the neuronal isoform of nitric oxide synthetase), the compound of Example 1 below gave an $IC_{50}$ of less than 10 $\mu$M indicating that it is expected to show useful therapeutic activity. In Screens B and C (the screens for activity against the macrophage and endothelial isoforms of nitric oxide synthetase) the compound of Example 1 gave $IC_{50}$ values more than 10 times that obtained in Screen A indicating that it shows desirable selectivity.

The compounds of Examples 2–9, 10(a)–(f), 11–13 and 19–24 were also tested in Screen A and also gave $IC_{50}$ values of less than 10 $\mu$M. Thus these compounds are also expected to show useful therapeutic activity.

Compounds of formula I, and pharmaceutically acceptable salts thereof, have the advantage that they are less toxic, more efficacious, more selective, are longer acting, have a broader range of activity, are more potent, produce fewer side effects, are more easily absorbed, or have other useful pharmacological properties than compounds previously known and used in the therapeutic fields mentioned above.

Compounds of formula I, and pharmaceutically acceptable salts thereof, may also have the advantage that they are more selective for the neuronal isoform of nitric oxide synthetase enzyme and are therefore expected to show useful therapeutic activity with a reduced side-effect profile associated with inhibition of the other isoforms.

The invention is illustrated by the following examples:

EXAMPLE 1

N-((2-(Phenylmethyl)amino)indan-5-yl)-2-thiophenecarboximidamide dioxalate (a) 5-Nitro-2-indanone This compound was prepared by the method of Heusier, Schieffer Ber., (1899) 32, 33.

(b) 5-Nitro-2-(Phenylmethyl)aminoindane

5-Nitro-2-indanone (1.48 g, 8.36 mmol), benzylamine (4.40 ml, 41.8 mmol), acetic acid (15.0 ml), 4 Å molecular sieves (20 ml), THF (15 ml), and MeOH (15 ml) were introduced into a flask and cooled to 0° C. Sodium cyanoborohydride (1.05 g, 16.7 mmol) was then added portionwise over a 5-minute period. The mixture was stirred for 14 hr, filtered through celite, and concentrated to a syrup. The mixture was made basic with 2N NaOH and extracted with ether (3×50 ml). The combined exacts were washed with water, dried over magnesium sulfate, filtered, concentrated and chromatographed over silica gel (3% methanol/methylene chloride) to yield 5-nitro-2-(phenylmethyl)aminoindane: (1.18 g, 53%); M.S. (M+H)$^+$=269.

(c) 2-(5-Nitroindanyl)-N-(phenylmethyl)trifluoroacetamide

To a stirred solution of 5-nitro-2-(phenylmethyl)aminoindane (1.18 g, 4.40 mmol) and triethylamine (0.61 ml, 4.40 mmol) in methylene chloride (50 ml) was added trifluoroacetic anhydride (0.63 ml, 4.40 mmol) dropwise. After stirring for 1 minute, the solvent was dumped into water and extracted with methylene chloride (3×20 ml). The combined extracts were washed with water, dried over magnesium sulfate, and filtered through a short plug of silica gel (20% ethyl acetate/hexane) to yield 2-(5-nitroindanyl)-N-(phenylmethyl)trifluoroacetamide: (1.17 g, 73%); M.S. (M+H)$^+$=365.

(d) 2-(5-Aminoindanyl)-W-(phenylmethyl)trifluoroacetamide

To a stirred solution of 2-(5-nitroindanyl)-N-(phenylmethyl)trifluoroacetamide (1.17g, 3.21 mmol) in THF/MeOH (100 ml, 1:1) was added a catalytic amount of 10% Pd/C. The mixture was hydrogenated at 50 psi for 1 hr, filtered through celite, and concentrated to give 2-(5-aminoindanyl)-N-(phenylmethyl)trifluoroacetamide which was homogeneous by TLC and used immediately in step (f).

(e) S-methyl-2-thiophenethiocarboximide hydroiodide

A solution of 2-thiophenecarboxthioamide (Maybridge Chemical) (11.1 g) in acetone (60 ml) was treated with iodomethane (13.4 g). After 6 hrs at 22° C., the resulting yellow solids were collected by filtration, washed with acetone (2×25 ml) and dried to provide 18.45 g of S-methyl-2-thiophenethiocarboximide hydroiodide, m.p.195° C. (dec).

(f) N-((2-(Phenylmethyl)amino)indan-5-yl)-2-thiophenecarboximidamide dioxalate

To a solution of 2-(5-aminoindamyl)-N-(phenylmethyl) trifluoroacetamide (1.0 g, 3.0 mmol) in isopropanol (6 ml)/DMF (0.5 ml) was added S-methyl-2-thiophenethiocarboximide hydroiodide (0.85 g, 3.0 mmol). The mixture was stirred for 14 hr, diluted with methanol (6 ml) and 2 N NaOH (6 ml) and heated to 50° C. for 0.5 hr. The mixture was dumped into water and extracted with ethyl acetate (3×30 ml). The combined extracts were washed with water, dried over magnesium sulfate, filtered, and chromatographed over silica gel (20% methanol/methylene chloride) to give the titled compound as the free base. Treatment with IPA/oxalic acid yielded N-((2-(phenylmethyl)amino)indan-5-yl)-2-thiophenecarboximidamide dioxalate as a white solid: (0.47 g, 30%); m.p. 130–135° C.

EXAMPLE 2

N-((2-(Phenylmethyl)amino)-1,2,3,4-tetrahydronaphth-7-yl)-2-thiophenecarboximidamide (a) 7-Nitro-3,4-dihydro-2(1H)-naphthaleneone This compound was prepared following the method of J. Med. Chem. (1989) 32, 2128.

(b) 7-Nitro-2-((phenylmethyl)amino)-1,2,3,4-tetrahydronaphthalene

7-Nitro-3,4-dihydro-2(1H)-naphthaleneone (1.50 g, 7.85 mmol), benzylamine (430 ml, 39.3 mmol), acetic acid (8.0 ml), 4 Å molecular sieves (20 ml), THF (15 ml), and MeOH (15 ml) were introduced into a flask and cooled to 0° C. Sodium cyanoborohydride (0.99 g, 15.7 mmol) was then added portionwise over a 5-minute period. The mixture was stirred for 14 hr, filtered through celite, and concentrated to a syrup. The mixture was made basic with 2N NaOH and extracted with ether (3×50 ml). The combined extracts were washed with water, dried over magnesium sulfate, filtered, concentrated and chromatographed over silica gel (3% methanol/methylene chloride) to yield 7-nitro-2-((phenylmethyl)amino)-1,2,3,4-tetrahydronaphthalene: (2.10 g, 95%); M.S. (M+H)$^+$=283.

(c) 2-(7-Nitro-(1,2,3,4-tetrahydronaphthyl))-N-(phenylmethyl))trifluoroacetamide To a stirred solution of 7-nitro-2-((phenylmethyl)amino)-1,2,3,4-tetrahydronaphthalene (2.10 g, 7.45 mmol) and triethylamine (1.07 ml, 7.45 mmol) in methylene chloride (50 ml) was added trifluoroacetic anhydride (1.05 ml, 7.45 mmol) dropwise. After stirring for 1 minute, the solvent was dumped into water and extracted with methylene chloride (3×20 ml). The combined extracts were washed with water, dried over magnesium sulfate, and filtered through a short plug of silica gel (20% ethyl acetate/hexane) to yield 2-(7-nitro-(1,2,3,4-tetrahydronaphthyl))-N-(phenylmethyl)trifluoroacetamide: (2.55 g, 90%): M.S. $(M+H)^+=379$.

(d) 2-(7-Amino-(1,2,3,4-tetrahydronaphthyl))-N-(phenylmethyl)trifluoroacetamide

To a stirred solution of 2-(7-nitro-(1,2,3,4-tetrahydronaphthyl))-N-(phenylmethyl)trifluoroacetamide (2.55 g, 6.75 mmol) in THF/MeOH (100 ml, 1:1) was added a catalytic amount of 10% Pd/C. The mixture was hydrogenated at 50 psi for 1 hr, filtered through celite, and concentrated to give 2-(7-amino-(1,2,3,4-tetrahydronaphthyl))-N-(phenylmethyl)trifluoroacetamide which was homogeneous by TLC and used immediately in the next step.

(e) N-((2-(Phenylmethyl)amino)-1,2,3,4-tetrahydronaphth-7-yl)-2-thiophenecarboximidamide To a solution of 2-(7-amino-(1,2,3,4-tetrahydronaphthyl))-N-(phenylmethyl)trifluoroacetamide (2.11 g, 6.07 mmol) in isopropanol (10 ml) was added S-methyl-2-thiophenethiocarboximide hydroiodide (1.72 g, 6.07 mmol). The mixture was stirred for 14 hr, diluted with methanol (6 ml) and 2 N NaOH (6 ml) and heated to 50° C. for 0.5 hr. The mixture was dumped into water and extracted with ethyl acetate (3×30 ml). The combined extracts were washed with water, dried over magnesium sulfate, filtered, and concentrated to a solid which was recrystallized (methylene chloride/hexane) to yield N-((2-(phenylmethyl)amino)-1,2,3,4-tetrahydronaphth-7-yl)-2-thiophenecarboximidamide as a white solid: (0.66 g, 30%); m.p. 119–120° C.

EXAMPLE 3

N-(2-Amino)-1,2,3,4-tetrahydronaphth-7-yl)-2-thiophenecarboximidamide dioxalate (a) 7-Nitro-2-amino-1,2,3,4-tetrahydronaphthalene hydrochloride 7-Nitro-1-tetralone (1.50 g, 7.85 mmol), ammonium acetate (6.05 ml, 78.5 mmol), acetic acid (8.0 ml), 4 Å molecular sieves (20 ml), THF (15 ml) and MeOH (15 ml) were introduced into a flask and cooled to 0° C. Sodium cyanoborohydride (0.99 g, 15.7 mmol) was then added portionwise over a 5-minute period. The mixture was stirred for 1 hr, filtered through celite, and concentrated to a syrup. The mixture was made basic with 2N NaOH and extracted with ether (3×50 ml). The combined extracts were washed with water, dried over magnesium sulfate, filtered, and concentrated to yield an oil. The compound was isolated as the hydrochloride salt 7-nitro-2-amino-1,2,3,4-tetrahydronaphthalene hydrochloride: (1.00 g, 56%); m.p. >300° C.

(b) 2-(7-Nitro-(1,2,3,4-tetrahydronaphthyl))-N-trifluoroacetamide

To a stirred solution of 7-nitro-2-amino-1,2,3,4-tetrahydronaphthalene hydrochloride (1.00 g, 4.39 mmol) and triethylamine (1.22 ml, 8.77 mmol) in methylene chloride (50 ml) was added trifluoroacetic anhydride (0.62 ml, 4.39 mmol) dropwise. After stirring for 1 minute, the solvent was dumped into water and extracted with methylene chloride (3×20 ml). The combined extracts were washed with water, dried over magnesium sulfate, and filtered through a short plug of silica gel (20% ethyl acetate/hexane) to yield 2-(7-nitro-(1,2,3,4-tetrahydronaphthyl))-N-trifluoroacetamide (0.78 g, 62%); M.S. $(M+H)^+=289$.

(c) 2-(7-Amino-(1,2,3,4-tetrahydronaphthyl))-N-trifluoroacetamide

To a stirred solution of 2-(7-nitro-(1,2,3,4-tetrahydronaphthyl))-N-trifluoroacetamide (0.76 g, 2.21 mmol) in THF/MeOH (100 ml, 1:1) was added a catalytic amount of 10% Pd/C. The mixture was hydrogenated at 50 psi for 1 hr, filtered through celite, and concentrated to give 2-(7-amino-(1,2,3,4-tetrahydronaphthyl))-N-trifluoroacetamide which was homogeneous by TLC and used immediately in the next reaction.

(d) N-(2-Amino)-1,2,3,4-tetrahydronaphth-7-yl)-2-thiophenecarboximidamide dihydrobromide To a solution of 2-(7-amino-(1,2,3,4-tetrahydronaphthyl))-N-trifluoroacetamide (0.70 g, 2.71 mmol) in isopropanol (10 ml) was added S-methyl-2-thiophenethiocarboximide hydroiodide (0.77 g, 2.71 mmol). The mixture was stirred for 14 hr, diluted with methanol (6 ml) and 2 N NaOH (6 ml) and heated to 50° C. for 0.5 hr. The mixture was dumped into water and extracted with ethyl acetate (3×30 ml). The combined extracts were washed with water, dried over magnesium sulfate, filtered, concentrated, and chromatographed over silica (20% methanol/methylene chloride) to yield an oil which was converted to the dihydrobromide salt: N-((2-amino)-1,2,3,4-tetrahydronaphth-7-yl)-2-thiophenecarboximidamide dihydrobromide: (0.37 g, 32%); dec >210° C.

EXAMPLE 4

N-((1-Amino)-1,2,3,4-tetrahydronaphth-7-yl)-2-thiophenecarboximidamide dioxalate (a) 7-Nitro-1-amino-1,2,3,4-tetrahydronaphthalene 7-Nitro-1-amino-1,2,3,4-tetrahydronaphthalene was made as for 7-Nitro-2-amino-1,2,3,4-tetrahydronaphthalene. The compound was isolated as the hydrochloride salt: (0.30 g, 12%); m.p. >300° C.

(b) 1-(7-Nitro-(1,2,3,4-tetrahydronaphthyl))-N-trifluoroacetamide 1-(7-Nitro-(1,2,3,4-tetrahydronaphthyl))-N-trifluoroacetamide was made as for 2-(7-nitro-(1,2,3,4-tetrahydronaphthyl))-N-trifluoroacetamide: (0.35 g, 95%); M.S. $(M+H)^+=289$.

(c) 1-(7-Amino-(1,2,3,4-tetrahydronaphthyl))-N-trifluoroacetamide 1-(7-Amino-1,2,3,4-tetrahydronaphthyl))-N-trifluoroacetamide was made as for 2(7-amino-(1,2,3,4-tetrahydronaphthyl))-N-trifluoroacetamide and used immediately in the next reaction.

(d) N-((1-Amino)-1,2,3,4-tetrahydronaphth-7-yl)-2-thiophenecarboximidamide dioxalate N-((1-Amino)-1,2,3,4-tetrahydronaphth-7-yl)-2-thiophenecarboximidamide dioxalate was made as for N-((2-amino)-1,2,3,4-tetrahydronaphth-7-yl)-2-thiophenecarboximidamide dihydrobromide except that it was isolated as the dioxalate salt: (0.18 g, 33%); dec >155° C.

EXAMPLE 5

N-((2-Amino)indan-5-yl)-2-thiophenecarboximidamide dioxalate (a) 5-Nitro-2-aminoindane hydrochloride To 2-aminoindane hydrochloride (19.11 g, 0.112 mol) at 0° C. was added sulfuric acid (60 ml) followed by potassium nitrate (11.84 g, 0.117 mol). The mixture was allowed to warm to room temperature, stirred for an additional 2 hr, then dumped onto ice/50% NaOH (500 ml total). The mixture was extracted with ether (3×200 ml) and the combined extracts were washed with water, dried over magnesium sulfate, filtered, and concentrated to an oil which was converted to the hydrochloride salt. Recrystallization from isopropanol/methanol afforded 5-nitro-2-aminoindane hydrochloride: (14.58 g, 60%); m.p. >300° C.

(b) 2-(5-Nitroindanyl)-N-trifluoroacetamide

To a stirred solution of 5-nitro-2-aminoindane hydrochloride (1.00 g, 5.89 mmol) and triethylamine (0.82 ml, 5.89 mmol) in methylene chloride (50 ml) was added trifluoroacetic anhydride (0.83 ml, 5.89 mmol) dropwise. After stirring for 1 minute, the solvent was dumped into water and extracted with methylene chloride (3×20 ml). The combined extracts were washed with water, dried over magnesium sulfate, and filtered through a short plug of silica gel (20% ethyl acetate/hexane) to yield 2-(5-nitroindanyl)-N-trifluoroacetamide: (1.51 g, 93%); m.p. 153–154° C.

(c) 2-(5-Aminoindanyl)-N-trifluoroacetamide

To a stirred solution of 2-(5-nitroindanyl)-N-trifluoroacetamide (0.58 g, 2.25 mmol) in THF/MeOH (100 ml, 1:1) was added a catalytic amount of 10% Pd/C. The mixture was hydrogenated at 50 psi for 1 hr, filtered through celite, and concentrated to give 2-(5-aminoindanyl)-N-trifluoroacetamide which was homogeneous by TLC and used immediately in the next step.

(d) N-((2-Amino)indan-5-yl)-2-thiophenecarboximidamide dioxalate

To a solution of 2-(5-aminoindanyl)-N-trifluoroacetamide (0.52 g, 2.25 mmol) in isopropanol (6 ml)/DMF (0.5 ml) was added S-methyl-2-thiophenethiocarboximide hydroiodide (0.64 g, 2.25 mmol). The mixture was stirred for 14 hr, diluted with methanol (6 ml) and 2 N NaOH (6 ml) and heated to 50° C. for 0.5 hr. The mixture was dumped into water and extracted with ethyl acetate (3×30 ml). The combined extracts were washed with water, dried over magnesium sulfate, filtered, and chromatographed over silica gel (20% methanol/methylene chloride) to give the titled compound as the free base. Treatment with IPA/oxalic acid yielded N-((2-amino)indane-5-yl)-2-thiophenecarboximidamide dioxalate as a white solid: (0.60 g, 50%); m.p. dec 70° C.

EXAMPLE 6

N-((2-(Methyl)(2-phenylmethyl)amino)indan-5-yl)-2-thiophenecarboximidamide dihydrobromide (a) 5-Nitro-2-(phenylmethyl)aminoindane hydrochloride To 5-nitro-2-aminoindane hydrochloride (3.00 g, 14.00 mmol) in DMF (60 ml) was added triethylamine (4.07 ml, 29.40 mmol) followed by benzyl bromide (1.74 ml, 14.68 mmol). The mixture was warmed to room temperature, stirred for 1 hr, dumped into water (200 ml), and extracted with ethyl acetate (3×50 ml). The combined extracts were washed with water, dried over magnesium sulfate, filtered through a small plug of silica gel and reduced to a syrup. The sub-titled compound was isolated as the hydrochloride salt: (2.29 g, 54%); m.p. dec 266° C.

(b) 5-Nitro-2-(methyl)(phenylmethyl)aminoindane hydrochloride

To 5-nitro-2-phenylmethyl)aminoindane hydrochloride (2.29 g, 7.52 mmol) in DMF (100 ml) was added potassium carbonate (260 g, 18.80 mmol) followed by methyl iodide (0.47 ml, 7.52 mmol). The mixture was warmed to room temperature, stirred for 16 hr, dumped into water (400 ml), and extracted with ethyl acetate (3×100 ml). The combined extracts were washed with water, dried over magnesium sulfate, filtered through a small plug of silica gel and reduced to a syrup. The titled compound was isolated as the hydrochloride salt: (1.08 g, 45%); m.p. dec 280° C.

(c) 5-Amino-2-(methyl)(phenylmethyl)aminoindane dihydrochloride

To 5-nitro-2-(methyl)(phenylmethyl)aminoindane hydrochloride (1.08 g, 339 mmol) in 85% acetic acid/water was added zinc powder (3.0 g). The mixture was stirred for 1 minute, filtered through celite and concentrated. The concentrate was neutralized with 2N NaOH and extracted with ethyl acetate (3×50 ml). The combined extracts were washed with water, dried over magnesium sulfate, and reduced to a syrup. The oil was treated with IPA/HCl, concentrated and used immediately in the next step.

(d) N-((2-(Methyl)(phenylmethyl)amino)indan-5-yl)-2-thiophenecarboximidamide dihydrobromide To 5-amino-2-(methyl)(phenylmethyl)aminoindane dihydrochloride in DMF (10 ml) was added S-methyl-2-thiophenethiocarboximide hydroiodide (0.98 g, 3.45 mmol) and pyridine (0.27 ml, 3.29 mmol). The mixture was stirred for 14 hr, dumped onto water/2N NaOH and extracted with ethyl acetate (3×50 ml). The combined extracts were washed with water, dried over magnesium sulfate, filtered, and chromatographed over silica gel (10% methanol/methylene chloride) to give the titled compound as the free base. Treatment with IPA/HBr yielded N-((2-(methyl)(phenylmethyl)amino)indan-5-yl)-2-thiophenecarboximidamide dihydrobromide as a white solid: (0.43 g, 25%); m.p. 196–200° C.

EXAMPLE 7

N-((1-amino)indane-6-yl)-2-thiophenecarboximidamide dihydrochloride (a) 6-Nitro-1-aminoindane hydrochloride 1-Aminoindane (10.0 g, 75.08 mmol) was added to concentrated sulfuric acid (40 ml) at 0° C. The mix was warmed to room temperature to aid in solvation then cooled to 0° C. Potassium nitrate (7.60 g, 75.08 mmol) was then added portionwise and the mixture allowed to stir at room temperature for 1 hr before being dumped onto ice/50% NaOH. The aqueous solution was extracted with chloroform (3×100 ml). The combined extracts were washed with water, decolorized with charcoal, dried over magnesium sulfate, filtered, and concentrated to an oil. Treatment with IPA/HCl afforded the subtitled compound: (6.90 g, 43%); m.p. dec 280° C.

(b) 6-Amino-1-aminoindane hydrochloride

To a solution of 6-nitro-1-aminoindane hydrochloride (1.00 g, 4.66 mmol) in MeOH (100 ml) was added a catalytic amount of 10% Pd/C. The mixture was hydrogenated at 50 psi for 1 hr, filtered through celite, and concentrated to give 6-amino-1-aminoindane hydrochloride which was homogeneous by TLC and used immediately in the next step.

(c) N-((1-amino)indan-6-yl)-2-thiophenecarboximidamide dihydrochloride

To 6-amino-1-aminoindane hydrochloride (0.74 g, 4.01 mmol) in DMF/IPA (4 ml, 1:1) was added S-methyl-2-thiophenethiocarboximide hydroiodide (1.26 g, 4.41 mmol). The mixture was heated to 50° C., stirred for 16 hr then dumped into water/2N NaOH and extracted with ethyl acetate (3×50 ml). The combined extracts were washed with water, dried over magnesium sulfate, filtered and concentrated to an oil. Treatment with IPA/HCl yielded N-((1-amino)indan-6-yl)-2-thiophenecarboximidamide dihydrochloride as a white solid: (0.79 g, 60%); m.p. dec >200° C.

EXAMPLE 8

N-((1-(Phenylmethyl)amino)indan-6-yl)-2-thiophenecarboximidamide dioxalate (a) 6-Nitro-1-(phenylmethyl)aminoindane hydrochloride To 6-nitro-1-aminoindane hydrochloride (1.90 g, 8.85 mmol) in DMF (30 ml) was added triethylamine (2.50 ml, 18.06 mmol) followed by benzyl bromide (1.07 ml, 9.03 mmol). The mixture was warmed to room temperature, stirred for 3 hr, dumped into water (100 ml), and extracted with ethyl acetate (3×70 ml). The combined extracts were washed with water, dried over magnesium sulfate, filtered through a small plug of silica gel and reduced to a syrup. The titled compound was isolated as the hydrochloride salt: (1.34 g, 50%); m.p. 234–235° C.

(b) 6-Amino-1-phenylmethyl)aminoindane hydrochloride

To 6-nitro-1-(phenylmethyl)aminoindane hydrochloride (1.34 g, 4.40 mmol) in MeOH (100 ml) was added a catalytic amount of 10% Pd/C. The mixture was hydrogenated at 50 psi for 1 hr, filtered through celite, and concentrated to give 6-amino-1-(phenylmethyl)aminoindane hydrochloride which was homogeneous by TLC and used immediately in the next step.

(c) N((2-(Phenylmethyl)amino)indan-6-yl)-2-thiophenecarboximidamide dioxalate

To 6-amino-1-(phenylmethyl)aminoindane hydrochloride (1.21 g, 4.40 mmol) in DMF (20 ml) was added S-methyl-2-thiophenethiocarboximide hydroiodide (1.38 g, 4.84 mmol). The mixture was heated to 50° C., stirred for 16 hr then dumped into water/2N NaOH and extracted with ethyl acetate (3×50 ml). The combined extracts were washed with water, dried over magnesium sulfate, filtered and concentrated to an oil. Treatment with IPA/oxalic acid yielded N-((1-(phenylmethyl)amino)indan-6-yl)-2-thiophenecarboximidamide dioxalate as a white solid: (1.06 g, 46%); m.p. dec >120° C.

EXAMPLE 9

N-((2-((3-Chlorophenyl)methyl)amino)indan-5-yl)-2-thiophenecarboxamidine (a) 2-((3-Chlorophenyl)carbonyl)amino-6-nitroindane To 2-amino-6-nitroindane hydrochloride (1.5 g, 7.0 mmol) in methylene chloride (50 ml) at 0° C. was added triethylamine (2.1 ml, 15.0 mmol) followed by 3-chlorobenzoyl chloride (1.0 ml, 7.5 mmol). The mixture was dumped immediately into water and the layers separated. The aqueous layer was extracted with methylene chloride (2×20 ml) and the combined extracts washed with water, dried over MgSO$_4$, filtered, and concentrated to an oil which was homogeneous by TLC and used immediately in the next step: M.S. (M+H)$^+$=317.

(b) 2-((3-Chlorophenyl)methyl)amino-6-nitroindane

To 2-((3-chlorophenyl)carbonyl)amino-6-nitroindane (2.2 g, 7.0 mmol) in THF (75 ml) was added BH$_3$•THF (1.0 M, 35 ml, 35 mmol) dropwise. The mixture was refluxed for 12 hr, cooled to 0° C., quenched with 4N HCl (60 ml), and refluxed for 1 hr. The resulting solution was evaporated to an oil, made basic with 50% NaOH, and extracted with methylene chloride (3×20 ml). The combined extracts were washed with water, dried over MgSO$_4$, filtered and concentrated to an oil. Treatment with IPA/HCl yielded 2-((3-chlorophenyl)methyl)amino-6-nitroindane: (2.1 g, 88% two steps); m.p. 234–237° C.

(c) 2-((3-chlorophenyl)methyl)amino-6-aminoindane

To 2-((3-chlorophenyl)methyl)amino-6-nitroindane hydrochloride (2.1 g, 6.13 mmol) in 85% AcOH/H$_2$O (40 ml) was added zinc metal (1.6 g, 24.5 mmol). The mixture was stirred for 5 min, filtered through celite, and evaporated to an oil. The oil was dumped into basic water and extracted with chloroform (3×20 ml). The combined extracts were washed with water, dried over MgSO$_4$, filtered and concentrated to an oil. Treatment with IPA/HCl yielded 2-((3-chlorophenyl)methyl)amino-6aminoindane: (1.5 g, 70%); m.p.>270° C.

(d) N-((2-((3-Chlorophenyl)methyl)amino)indan-5-yl)-2-thiophenecarboxamidine 2-((3-Chlorophenyl)methyl)amino-6-aminoindane dihydrochloride (1.5 g, 4.2 mmol), S-methyl-2-thiophenethiocarboximide hydroiodide (1.3 g, 4.6 mmol) and pyridine (0.34 ml, 4.2 mmol) in DMF (10 ml) were stirred for 24 hr. The mixture was dumped into water, made basic with 2N NaOH and extracted with ethyl acetate (3×50 ml). The combined extracts were washed with water, dried over MgSO$_4$, filtered, concentrated, and chromatographed over silica gel (12% MeOH/methylene chloride) to afford a colorless oil. Treatment with IPA/HCl yielded N-((2-((3-chlorophenyl)methyl)amino)indan-5-yl)-2-thiophenecarboxamidine: (0.75 g, 40%); m.p. 297–299° C.

EXAMPLE 10

The following compounds were prepared according to the method of Example 9:

(a) N-((2-((2-Methylphenyl)methyl)amino)indan-5-yl)-2-thiophenecarboxamidine; m.p. 183° C.
(b) N-((2-((3-Methylphenyl)methyl)amino)indan-5-yl)-2-thiophenecarboxamidine; m.p. 195° C.
(c) N-((2-((4-Methylphenyl)methyl)amino)indan-5-yl)-2-thiophenecarboxamidine; m.p. 182° C.
(d) N-((2-(Ethyl)amino)indan-5-yl)-2-thiophenecarboxamidine; m.p. 236–238° C.
(e) N-((2-(((4-Phenyl)phenyl)methyl)amino)indan-5-yl-2-thiophenecarboxamidine; m.p. 182° C.
(f) N-((2-(((4-Hexyl)phenyl)methyl)amino)indan-5-yl)-2-thiophenecarboxamidine; m.p. 125° C.
(g) N-((2-((3-Bromophenyl)methyl)amino)indan-5-yl-2-thiophenecarboxamidine; m.p. 182° C.

EXAMPLE 11

N-((2-((3-Chlorophenyl)methyl)amino)-1,2,3,4-tetrahydronaphth-7-yl)-2-thiophenecarboximidamide (a) 7-Nitro-2-(((3-chlorophenyl)methyl)amino)-1,2,3,4-tetrahydronaphthalene 7-Nitro-3,4-dihydro-2(1H)-naphthaleneone (1.50 g, 7.85 mmol), 3-chlorobenzylamine (4.70 ml, 39.3 mmol), acetic acid (6.0 ml), 4 Å molecular sieves (20 ml), THF (15 ml), and MeOH (15 ml) were introduced into a flask and cooled to 0° C. Sodium cyanoborohydride (0.99 g, 15.7 mmol) was added portionwise over a 5-minute period. The mixture was stirred for 14 hr, filtered through celite, and concentrated to a syrup. The mixture was made basic with 2N NaOH and extracted with ether (3×50 ml). The combined extracts were washed with water, dried over magnesium sulfate, filtered, concentrated and chromatographed over silica gel (3% methanol/methylene chloride). Treatment of the oil with IPA/HCl yielded 7-nitro-2-(((3-chlorophenyl)methyl)amino)-1,2,3,4-tetrahydronaphthalene hydrochloride: (1.34 g, 50%); M.S. (M+H)$^+$=317.

(b) 7-Amino-2-(((3-chlorophenyl)methyl)amino)-1,2,3,4-tetrahydronaphthalene

To 7-nitro-2-(((3-chlorophenyl)methyl)amino)-1,2,3,4-tetrahydronaphthalene hydrochloride (1.34 g, 3.80 mmol) in 85% AcOH/H$_2$O (75 ml) was added zinc metal (2.48 g, 38.0 mmol). The mixture was stirred for 5 min. filtered through celite, and evaporated to an oil. The oil was dumped into basic water and extracted with chcloroform (3×20 ml). The combined extracts were washed with water, dried over MgSO$_4$, filtered and concentrated to an oil. Treatment with IPA/HCl yielded 7-amino-2-(((3-chlorophenyl)methyl)amino)-1,2,3,4-tetrahydronaphthalene (1.4 g, 99%); M.S. (M+H)$^+$=288.

(c) N-((2-((3-Chlorophenyl)methyl)amino)-1,2,3,4-tetrahydronaphth-7-yl)-2-thiophenecarboximidamide 7-Amino-2-(((3-chlorophenyl)methyl)amino)-1,2,3,4-tetrahydronaphthalene dihydrochloride (1.32 g, 3.70 mmol), S-methyl-2-thiophenethiocarboximide hydroiodide (1.3 g, 4.6 mmol), and pyridine (0.30 ml, 3.7 mmol) in DMF (15 ml) were stirred for 24 hr. The mixture was dumped into water, made basic with 2N NaOH and extracted with ethyl acetate (3×50 ml). The combined extracts were washed with water, dried over MgSO$_4$, filtered and concentrated to an oil. Treatment with IPA/oxalic acid yielded N-((2-((3-chlorophenyl)methyl)amino)-1,2,3,4-tetrahydronaphth-7-yl)-2-thiophenecarboximidamide dioxalate: (0.71 g, 33%); dec >100° C.

EXAMPLE 12

N-((2-(Phenylmethyl)(methyl)amino)-1,2,3,4-tetrahydronaphth-7-yl)-2-thiophenecarboximidamide (a) 7-Nitro-2-((2-phenylmethyl)(methyl)amino)-1,2,3,4-tetrahydronaphthalene To a stirred solution of 7-nitro-2-((phenylmethyl)amino)-1,2,3,4-tetrahydronaphthalene (1.5 g, 5.4 mmol) in DMF (30 ml) was added potassium carbonate (1.5 g, 10.8 mmol) and methyl iodide (0.36 ml, 5.8 mmol). The mixture was stirred for 24 hr, dumped into water and extracted with ethyl acetate (3×50 ml). The combined extracts were washed with water, dried over MgSO$_4$, filtered and concentrated to an oil. Treatment with IPA/HCl yielded 7-nitro-2-((phenylmethyl)(methyl)amino)-1,2,3,4-tetrahydronaphthalene hydrochloride: (0.89 g, 50%); M.S. (M+H)$^+$=297.

(b) 7-Amino-2-((phenylmethyl)(methyl)amino)-1,2,3,4-tetrahydronaphthalene

To 7-nitro-2-((phenylmethyl)(methyl)amino)-1,2,3,4-tetrahydronaphthalene hydrochloride (0.89 g, 2.7 mmol) in 85% AcOH/H$_2$O (75 ml) was added zinc metal (3.5 g, 54.0 mmol). The mixture was stirred for 5 min, filtered through celite, and evaporated to an oil. The oil was dumped into basic water and extracted with chloroform (3×20 ml). The combined extracts were washed with water, dried over MgSO$_4$, filtered and concentrated to an oil. Treatment with IPA/HCl yielded 7-amino-2-((phenyl)methyl)(methyl)amino)-1,2,3,4-tetrahydronaphthalene: (0.81 g, 88%); M.S. (M+H)$^+$=267.

(c) N-((2-(Phenylmethyl)(methyl)amino)-1,2,3,4-tetrahydronaphth-7-yl)-2-thiophenecarboximidamide 7-Amino-2-((phenylmethyl)(methyl)amino)-1,2,3,4-tetrahydronaphthalene dihydrochloride (0.81 g, 2.4 mmol), S-methyl-2-thiophenethiocarboximide hydroiodide (0.74 g, 2.6 mmol) and pyridine (0.19 ml, 2.4 mmol) in DMF (15 ml) were stirred for 24 hr. The mixture was dumped into water, made basic with 2N NaOH and extracted with ethyl acetate (3×50 ml). The combined extracts were washed with water, dried over MgSO$_4$, filtered, concentrated and chromatographed over silica gel (15% MeOH/methylene chloride). Concentration of the fractions yielded a solid which was recrystallized from ethyl acetate/hexane affording N-((2-(phenylmethyl)(methyl)amino)-1,2,3,4-tetrahydronaphth-7-yl)-2-thiophenecarboximidamide dihydrochloride: (0.14 g, 16%); m.p 176–178° C.

EXAMPLE 13

N-((1-(Phenylmethyl)amino)-1,2,3,4-tetrahydronaphth-7-yl)-2-thiophenecarboximidamide (a) 7-Nitro-1-((phenylmethyl)amino)-1,2,3,4-tetrahydronaphthalene 7-Nitro-1-tetralone (2.0 g, 10.5 mmol), benzylamine (1.2 ml, 10.5 mmol) and titanium isopropoxide (3.9 ml, 13.1 mmol) were combined and stirred for 1 hr. The mixture was diluted with absolute ethanol (12 ml), treated with sodium cyanoborohydride (0.44 g, 7.0 mmol) and allowed to stir for 20 hr. The solids were filtered and washed with ethanol. The ethanol was concentrated and the remaining oil used immediately in the next reaction: M.S. (M+H)$^+$=283.

(b) 1-(7-Nitro-(1,2,3,4-tetrahydronaphthyl))-N-(phenylmethyl)trifluoroacetamide

To a stirred solution of 7-nitro-1-((phenylmethyl)amino)-1,2,3,4-tetrahydronaphthalene (2.96 g, 10.50 mmol) and triethylamine (1.46 ml, 10.50 mmol) in methylene chloride (50 ml) was added trifluoroacetic anhydride (1.46 ml, 10.50 mmol) dropwise. After stirring for 1 minute, the solvent was dumped into water and extracted with methylene chloride (3×20 ml). The combined extracts were washed with water, dried over magnesium sulfate, and filtered through a short plug of silica gel (20% ethyl acetate/hexane) to yield 1-(7-nitro-(1,2,3,4-tetrahydronaphthyl))-N-(phenylmethyl)trifluoroacetamide: (1.90 g, 48% two steps); M.S. (M+H)$^+$=379.

(c) 1-(7-Amino-(1,2,3,4-tetrahydronaphthyl))-N-(phenylmethyl)trifluoroacetamide

To a stirred solution of 1-(7-nitro-(1,2,3,4-tetrahydronaphthyl))-N-(phenylmethyl)trifluoroacetamide (1.91 g, 5.05 mmol) in THF/MeOH (100 ml 1:1) was added a catalytic amount of 10% Pd/C. The mixture was hydrogenated at 50 psi for 1 hr, filtered through celite, and concentrated to give 1-(7-amino-(1,2,3,4-tetrahydronaphthyl))-N-(phenylmethyl)trifluoroacetamide which was homogeneous by TLC and used immediately in the next step.

(d) N-((1-(Phenylmethyl)amino)-1,2,3,4-tetrahydronaphth-7-yl)-2-thiophenecarboximidamide To a solution of 1-(7-amino-(1,2,3,4-tetrahydronaphthyl))-N-(phenylmethyl)trifluoroacetamide (1.76 g, 5.05 mmol) in isopropanol (10 ml) was added S-methyl-2-thiophenethiocarboximide hydroiodide (1.44 g, 5.05 mmol). The mixture was stirred for 14 hr, diluted with methanol (6 ml) and 2 N NaOH (6 ml) and heated to 50° C. for 0.5 hr. The mixture was dumped into water and extracted with ethyl acetate (3×30 ml). The combined extracts were washed with water, dried over magnesium sulfate, filtered, and concentrated to an oil. Treatment with IPA/HBr yielded N-((2-(phenylmethyl)amino-1,2,3,4-tetrahydronaphth-7-yl)-2-thiophenecarboximidamide dihydrobromide as a white solid: (0.53 g, 20%); m.p. 260–262° C.

EXAMPLE 14

N-((1-(Phenylmethyl)amino)indan-5-yl)-2-thiophenecarboximidamide (a) 6-Acetamido-(1-((phenyl)methyl)amino)indane 6-Acetamido-1-indanone (5.0 g, 27.6 mmol), benzylamine (3.1 ml 27.9 mmol), and titanium isopropoxide (10.2 ml, 34.5 mmol) were combined and stirred for 1 hr. The mixture was diluted with absolute ethanol (30 ml), treated with sodium cyanoborohydride (1.2 g, 19.3 mmol) and allowed to stir for 20 hr. The solids were filtered and washed with ethanol. The ethanol was concentrated and the remaining oil dissolved in ethyl acetate and extracted with 1N HCl (3×50 ml). The aqueous layer was neutralized with 2N NaOH and extracted with ethyl acetate (3×100 ml). The combined extracts were washed with water, dried over magnesium sulfate, filtered, and concentrated to an oil which was used without purification in the next step.

(b) 6-Amino-(1-((phenyl)methyl)amino)indane

6-Acetamido-(1-((phenyl)methyl)amino)indane was refluxed in 4N HCl (50 ml) for 20 min, cooled and extracted with ethyl acetate (3×50 ml). The aqueous layer was neutralized with 2N NaOH and extracted with ethyl acetate (3×100 ml). The combined extracts were washed with water, dried over magnesium sulfate, filtered and concentrated to an oil. The oil was dissolved in IPA and treated with IPA/HCl yielding the dihydrochloride salt: (2.0 g, 24% for two steps); m.p. dec >250° C.

(c) N-((1-(Phenylmethyl)amino)indan-5-yl)-2-thiophenecarboximidamide

To 6-amino-(1-((phenyl)methyl)amino)indane dihydrochloride (2.0 g, 6.4 mmol) in DMF (20 ml) was added S-methyl-2-thiophenethiocarboximide hydroiodide (2.2 g, 7.7 mmol) and pyridine (0.57 ml, 7.1 mmol). The mixture was stirred at 50° C. for 20 hr, dumped into basic water and extracted with ethyl acetate (3×100 ml). The combined extracts were washed with water, dried over magnesium sulfate, filtered, concentrated and chromatographed over silica gel (6% methanol/methylene chloride). The extracts were concentrated to an oil which was dissolved in methanol, treated with IPA/HCl and triturated with ether. The solids were collected by filtration and washed with ether: (1.1 g, 40%); m.p. dec >180° C.

EXAMPLE 15

The following compound was prepared following the method of Example 14: N-((1-(Phenylmethyl)amino)-1,2,3,4-tetrahydronaphth-6-yl)-2-thiophenecarboximidamide m.p. dec >200° C.

EXAMPLE 16

N-((2-(Phenylmethyl)amino)-1,2,3,4-tetrahydronaphth-7-yl)-2-furancarboximidamide (a) 2-((Phenyl)carbonyl)amino-7-nitrotetralin To 2-amino-7-nitrotetralin (2.8 g, 14.5 mmol) in THF (50 ml) and 10% $K_2CO_3$ (100 ml) was added benzoyl chloride (1.7 mm 15.3 mmol). After the addition was complete, the mixture was diluted with water to a volume of 250 ml. The precipitated solids were collected by filtration, washed with water, and dried in vacuo: (4.2 g, 98%), m.p. 194–198° C.

(b) 2-((Phenyl)methyl)amino-7-nitrotetralin hydrochloride

To 2-((phenyl)carbonyl)amino-7-nitrotetralin (4.2 g, 14.1 mmol) in anhydrous THF (100 ml) was added borane-THF (49.3 ml, 1M THF, 49.3 mmol). The mixture was refluxed for 5 hr, cooled to 0° C., and quenched with the dropwise addition of 4N HCl. The mixture was again brought to reflux for 1 hr, concentrated in vacuo, and the solids filtered (washed with water) and dried in vacuo: (3.5 g, 78%), m.p. >300° C.

(c) 2-((Phenyl)methyl)amino-7-aminotetralin hydrochloride

To a stirred solution of 2-((phenyl)methyl)amino-7-nitrotetralin (2.0 g, 6.3 mmol) in MeOH (100 ml) was added a catalytic amount of 10% Pd/C. The mixture was hydrogenated at 50 psi for 1 hr, filtered through celite, and concentrated to an oil which was homogeneous by TLC and used immediately in the next step.

(d) N-((2-(Phenylmethyl)amino)-1,2,3,4-tetrahydronaphth-7-yl)-2-furancarboximidamide To 2-((phenyl)methyl)amino-7-aminotetralin hydrochloride (1.8 g, 6.3 mmol) in DMF (20 ml) was added S-methyl-2-furanthiocarboximide hydroiodide (2.0 g, 7.5 mmol). The mixture was stirred for 2 hr at 45° C., dumped into basic water and extracted with ethyl acetate (3×100 ml). The combined extracts were washed with water, dried over magnesium sulfate, filtered and concentrated to an oil. The oil was dissolved in methanol, treated with IPA/HCl and triturated with ether. The solids were collected by filtration and washed with ether (2.2 g, 84%), m.p. dec >195° C.

Preparation of Chiral Intermediate Compounds for Examples 17 and 18

Resolution of 2-amino-7-nitrotetralin

2-Amino-7-nitrotetralin (30 g, 156 mmol) dissolved in 200 ml of acetone was added to dibenzoyl-D-tartaric acid (58.7 g, 164 mmol) also dissolved in 200 ml of acetone. The thick paste was filtered and washed with acetone. The paste was refluxed in 3 L of water/ethanol/acetonitrile (1:1:1) then filtered hot. The solids collected upon filtration were recrystallized from the above mixture (3×): (525 g, 6%) of a single isomer was obtained as determined by chiral capillary zone electrophorisis, m.p. 240–242° C.

Likewise, dibenzoyl-L-tartaric acid could be employed to resolve the opposite enantiomer using the same solvent system as that described above: (5.3 g, 6%), of a single isomer was obtained as determined by chiral capillary zone electrophorisis, m.p. 240–242° C.

EXAMPLE 17

(+)-N-((2-((Phenyl)methyl)amino)-1,2,3,4-tetrahydronaphth-7-yl)-2-thiophenecarboximidamide (a) (+)-2-((Phenyl)carbonyl)amino-7-nitrotetralin To 2-amino-7-nitrotetralin (1.8 g, 9.39 mmol, derived from dibenzoyl-D-tartaric acid) in THF (50 ml) and 10% $K_2CO_3$ (100 ml) was added benzoyl chloride (1.2 ml, 10.1 mmol). After the addition was complete, the mixture was diluted with water to a volume of 250 ml. The precipatated solids were collected by filtration, washed with water and dried in vacuo: (2.8 g, 100%), m.p. 208–209° C., $[a]_D$ +21.9° (c 0.33 DMSO).

(b) (+)-2-((phenyl)methyl)amino-7-nitrotetralin hydrochloride

To (+)-2-((phenyl)carbonyl)amino-7-nitrotetralin (2.8 g, 9.4 mmol) in anhydrous THF (100 ml) was added borane-THF (32.8 ml, 1M THF, 32.8 mmol). The mixture was refluxed for 5 hr, cooled to 0° C., and quenched with the dropwise addition of 4N HCl. The mixture was brought to reflux for 1 hr, concentrated in vacuo, and the solids filtered (washed with water) and dried in vacuo: (2.8 g, 94%), m.p. >300° C., $[a]_D$ +51.0° (c 0.33 DMSO).

(c) (+)-2-((Phenyl)methyl)amino-7-aminotetralin hydrochloride

To a stirred solution of (+)-2-((phenyl)methyl)amino-7-nitrotetralin (2.8 g, 8.7 mmol) in MeOH (100 ml) was added a catalytic amount of 10% Pd/C. The mixture was hydrogenated at 50 psi for 1 hr, filtered through celite, and concentrated to a glassy solid which was homogeneous by TLC; $[a]_D$ +73.3° (c 0.87 DMSO).

(d) (+)-N-(2-(Phenylmethyl)amino)-1,2,3,4-tetrahydronaphth-7-yl)-2-thiophenecarboximidamide To (+)-2-((phenyl)methyl)amino-7-aminotetralin hydrochloride (2.5 g, 8.7 mmol) in DMF (20 ml) was added S-methyl-2-thiophenethiocarboximide hydroiodide (3.0 g, 10.4 mmol). The mixture was stirred for 4 hr at 45° C., dumped into basic water and extracted with ethyl acetate (3×100 ml). The combined extracts were washed with water, dried over magnesium sulfate, filtered, and concentrated to an oil. The oil was dissolved in methanol, treated with IPA/HCl and triturated with ether. The solids were collected by filtration and washed with ether. One recrystallization from IPA/MeOH/Et$_2$O yielded a white solid: (2.5 g, 66%), m.p. dec >260° C., [a]$_D$ +44.5° (c 0.62 DMSO).

EXAMPLE 18

(−)-N-((2-((Phenyl)methyl)amino)-1,2,3,4-tetrahydronaphth-7-yl)-2-thiophenecarboximidamide (a) (−)-2-((Phenyl)carbonyl)amino-7-nitrotetralin To 2-amino-7-nitrotetralin (1.8 g, 9.39 mmol, derived from dibenzoyl-L-tartaric acid) in THF (50 ml) and 10% K$_2$CO$_3$ (100 ml) was added benzoyl chloride (1.2 ml, 10.1 mmol). After the addition was complete, the mixture was diluted with water to a volume of 250 ml. The precipitated solids were collected by filtration, washed with water and dried in vacuo: (2.8 g, 100%), m.p. 208–209° C., [a]$_D$ −24.0° (c 0.87 DMSO).

(b) (−)-2-((phenyl)methyl)amino-7-nitrotetralin hydrochloride

To (−)-2-((phenyl)carbonyl)amino-7-nitrotetralin (2.8 g, 9.4 mmol) in anhydrous THF (100 ml) was added borane-THF (32.8 ml, 1M THF, 32.8 mmol). The mixture was refluxed for 5 hr, cooled to 0° C., and quenched with the dropwise addition of 4N HCl. The mixture was again brought to reflux for 1 hr, concentrated in vacuo, and the solids filtered (washed with water) and dried in vacuo: (2.8 g, 94%), m.p. >300° C., [a]$_D$ −59.4° (c 0.39 DMSO).

(c) (−)-2-((Phenyl)methyl)amino-7-aminotetralin hydrochloride

To a stirred solution of (−)-2-((phenyl)methyl)amino-7-nitrotetralin (2.8 g, 8.7 mmol) in MeOH (100 ml) was added a catalytic amount of 10% Pd/C. The mixture was hydrogenated at 50 psi for 1 hr, filtered through celite and concentrated to a glassy solid which was homogeneous by TLC; [a]$_D$ −74.6° (c 0.80 DMSO).

(d) (−)-N-((2-Phenylmethyl)amino)-1,2,3,4-tetrahydronaphth-7-yl)-2-thiophenecarboximidamide To (−)-2-((phenyl)methyl)amino-7-aminotetralin hydrochloride (2.5 g, 8.7 mmol) in DMF (20 ml) was added S-methyl-2-thiophenethiocarboximide hydroiodide (3.0 g, 10.4 mmol). The mixture was stirred for 4 hr at 45° C., dumped into basic water and extracted with ethyl acetate (3×100 ml). The combined extracts were washed with water, dried over magnesium sulfate, filtered and concentrated to an oil. The oil was dissolved in methanol treated with IPA/HCl and triturated with ether. The solids were collected by filtration and washed with ether. One recrystallization from IPA/MeOH/Et$_2$O yielded a white solid: (2.7 g, 71%), m.p. dec >260° C., [a]$_D$ −44.5° (c 0.57 DMSO).

EXAMPLE 19

N-(2,3,4,5-Tetrahydro-1H-3-benzazepine-7-yl)thiophene-2-carboximidamide (a) 2,3,4,5-Tetrahydro-1H-3-benzazepin-7-amine monohydrochloride To a solution of 2,3,4,5-tetrahydro-7-nitro-1H-3-benzazepine hydrochloride (1.68 g, 7.35 mmol) in ethanol (100 ml) was added 5% palladium on carbon (0.2 g) and the solution was placed on a Paar Hydrogenator Apparatus and pressurized with 45 psi of hydrogen. After the theoretical uptake of hydrogen had been achieved (2 h), the catalyst was filtered off and washed with water (25 ml). The filtrate was concentrated. Absolute ethanol was added and evaporated until all of the water had been evaporated and a solid formed. The solid was dissolved in hot ethanol (50 ml) and the product was precipitated by the addition of ether (75 ml). The solid was collected and air-dried to give the product as an off-white solid (2.43 g (94%)), m.p. 288–91° C.

N-(2,3,4,5-tetrahydro-1H-3-benzazepine-7-yl)thiophene-2-carboximidamide

A suspension of 2,3,4,5-tetrahydro-1H-3-benzazepin-7-amine monohydrochloride (0.60 g, 3.0 mmol) and of S-methyl 2-thiophenethiocarboximide hydroiodide (1.1 g, 3.8 mmol) in dimethyl formamide (2.0 ml) and isopropanol (2.0 ml) was stirred at ambience for 20 h. The solid from the reaction was collected and washed with isopropanol (5 ml) and ethyl acetate (15 ml). The air-dried solid weighed 1.18 g and was a mixed salt. This solid was dissolved in water and was basified and extracted into ethyl acetate. The solvent was dried over magnesium sulfate and concentrated to give the free base as a yellow solid. This was taken up in isopropanol (30 ml) and acidified with hydrogen bromide in isopropanol until the solution was acidic. The product was precipitated by the addition of ethyl acetate (35 ml). The product was collected and was dried to give the product as the dihydrobromide salt (0.70 g (54%)), m.p. 281–3° C.

EXAMPLE 20

N-(1,2,3,4-Tetrahydroisoquinoline-7-yl)thiophene-2-carboximidamide (a) 1,2,3,4-Tetrahydroisoquinolin-7-amine monohydrochloride This was prepared following the method of Example 19, step (a). From 7-nitro-1,2,3,4-tetrahydroisoquinoline hydrochloride (3.00 g, 14.0 mmol) and 5% palladium on carbon (0.3 g) in ethanol (150 ml) was isolated product as a light rose colored solid (2.43 g (94%)), m.p. 232–4° C.

(b) N-(1,2,3,4-tetrahydroisoquinoline-7-yl)thiophene-2-carboximidamide

This was prepared following the method of Example 19, step (b). From 1,2,3,4-tetrahydroisoquinolin-7-amine monohydrochloride (0.46 g) and S-methyl 2-thiophenethiocarboximide hydroiodide (0.85 g) in isopropanol (2.0 ml) and dimethyl formamide (2.0 ml) was isolated after workup the title compound as the free base (0.60 g (94%)). This was converted to the bisoxalate salt in a methanol/ethyl acetate solution to give the product as an off-white solid (0.59 g (54%)), m.p. 199–200° C. (dec).

EXAMPLE 21

N-(2-benzyl-1,2,3,4-tetrahydroisoquinoline-7-yl)thiophene-2-carboximidamide (a) 2-benzyl-7-nitro-1,2,3,4-tetrahydroisoquinoline monohydrochloride To a solution of 7-nitro-1,2,3,4-tetrahydroisoquinoline monohydrochloride (2.50 g, 11.6 mmol) and potassium carbonate (2.0 g) in acetonitrile (100 ml) was added benzyl bromide (2.22 g, 13.0 mmol) in acetonitrile (10 ml). The solution was stirred overnight and the solid was then removed by filtration. The solvent was removed in vacuo to give a solid which was partitioned between methylene chloride and water. The dried (MgSO$_4$) organic phase was concentrated and the resulting oil was taken up in ethanol (50 ml). This solution was made acidic with hydrochloric acid in ethanol. The precipitate which formed had set up solid and an additional 150 ml of ethanol and 50 ml of ether was added. The solid was collected and air dried to give 2-benzyl-7-nitro-1,2,3,4-tetrahydroisoquinoline hydrochloride as an off white solid (2.78 g (79%)), m.p. 256–8° C. (dec).

(b) 2-benzyl-1,2,3,4-tetrahydroisoquinolin-7-amine hydrochloride

This compound was prepared following the method of Example 19, step (a). From 2-benzyl-7-nitro-1,2,3,4-tetrahydroisoquinoline hydrochloride (2.00 g, 6.56 mmol) and 5% palladium on carbon (0.2 g) in ethanol (100 ml) was isolated the product as a yellow colored solid (1.05 g (78%)), m.p. 257–9° C. (dec).

(c) N-(2-benzyl-1,2,3,4-tetrahydroisoquinoline-7-yl)thiophene-2-carboximidamide

This was prepared following the method of Example 19, step (b). From 2-benzyl-1,2,3,4-tetrahydroisoquinolin-7-amine monohydrochloride (0.50 g, 1.8 mmol) and S-methyl 2-thiophenethiocarboximide hydroiodide (0.67 g, 2.3 mmol) in isopropanol (2.0 ml) and dimethyl formamide (2.0 ml) was isolated the title compound as a yellow solid (0.53 g (84%)). This was converted to the oxalate salt in isopropanol, m/e=348 (M+H).

EXAMPLE 22

N-(1,2,3,4-tetrahydroisoquinolin-5-yl)thiophene-2-carboximidamide, dioxalate salt This compound was prepared by following a process analogous to that described above in Example 20. m.p. 75° C. (dec).

EXAMPLE 23

N-(1,2,3,4-tetrahydroisoquinoline-6-yl)thiophene-2-carboximidamide (a) 1,2,3,4-tetrahydroisoquinoline-6-amine monohydrochloride A solution of isoquinolin-6-amine [Manske, R. H. F., et. al., *J. Am. Chem. Soc.*, 72, 4997 (1950)] (4.40 g, 30.5 mmol) and platinum oxide (300 mg) in a solution of acetic acid (85 ml) and 2.5 M hydrochloric acid (30 ml) was placed on a Paar Hydrogenator Apparatus and was pressurized with 45 psi of hydrogen for 16 h, The solvent was removed in vacuo and the resulting salt was partitioned between aqueous potassium carbonate and 20% isopropanol in methylene chloride. The dried (magnesium sulfate) organic phase was concentrated and the resulting oil was chromatographed on silica gel using 2% methanol in chloroform as eluent to give 3.08 g (93%) of the product as an oily solid. This product (3.08 g, 20.8 mmol) was taken up in 200 ml of ethanol and 1 equivalent of a 0.1000 M hydrochloric acid solution was added. The solvent was removed to yield the monohydrochloride as a solid, MS 149 (M+H).

(b) N-(1,2,3,4-tetrahydroisoquinoline-6-yl)thiophene-2-carboximidamide

This was prepared following the method of Example 19, step (b). From 1,2,3,4-tetrahydroisoquinoline-6-amine monohydrochloride (0.90 g, 4.9 mmol) and S-methyl 2-thiophenethiocarboximide hydroiodide (1.80 g, 6.2 mmol) in isopropanol (2.0 ml) and dimethyl formamide (2.0 ml) was isolated after workup and chromatography on silica gel the title compound as the free base (0.74 g (57%)), m.p. 170–5° C.

EXAMPLE 24

N-(2-Isoquinolin-7-yl)thiophene-2-carboximidamide (a) 7-Nitroisoquinoline

A solution of 7-nitro-3,4-dihydroisoquinoline (3.00 g, 17.0 mmol) and 5% palladium on carbon (3.0 g) in decalin (75 ml) was heated at reflux for 3 h. Upon cooling, the solution was filtered and the catalyst washed with chloroform (200 ml). The solvent was removed in vacuo to give 7-nitroisoquinoline (1.63 g) as a tan solid. MS 175 (M+H).

(b) Isoquinolin-7-amine

7-Nitroisoquinoline (1.62 g, 9.25 mmol) in ethanol (150 ml) was hydrogenated on a Paar Hydrogenator Apparatus over 5% palladium on carbon (0.2 g) as catalyst for 3 h at 50 psi. The reaction mixture was filtered and the solvent removed at reduced pressure. Recrystallization of the solid from ethanol (3 ml) gave isoquinolin-7-amine (0.98 g) as a tan solid. MS 145 (M+H), NMR (CDCl$_3$) 9.02 (s, 1H), 8.29 (d, 1H), 7.63 (d, 1H), 7.47 (d, 1H),7.13 (dd, H), 7.03 (d, 1H), 4.00 (broad, 2H).

(c) N-(Isoquinolin-7-yl)thiophene-2-carboximidamide

A solution of isoquinolin-7-amine (0.96 g, 6.7 mmol) and S-methyl 2-thiophenethiocarboximide (2.42 g, 8.36 mmol) in isopropanol (4 ml) and DMF (4 ml) was stirred for 18 h. The solution was poured into dilute sodium hydroxide and extracted with methylene chloride. The extract was dried over magnesium sulfate and the solvent evaporated to give and oil which solidified on standing. The sample was purified by column chromatography on silica gel (5% methanol in chloroform saturated with gaseous ammonia) to give 1.31 g of a solid. The solid was recrystallized from ethyl acetate (25 ml) to give 1.05 g of the title compound as an off-white solid, m.p. 177.5–8.5° C.

What is claimed is:

1. A method of treatment or prophylaxis of diseases or conditions in which preferential inhibition of the neuronal isoform of NOS is beneficial which comprises administering to a person in need thereof a therapeutically effective amount of a compound of formula (I)

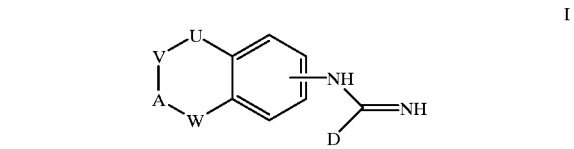

wherein
D represents a five membered heterocyclic aromatic ring containing 1 to 4 heteroatoms selected from O, N or S, optionally substituted at a carbon atom by halogen, trifluoromethyl, alkyl C1 to 6, nitro, cyano, and which is connected to the remainder of the compound of formula I through a carbon atom;
A represents N(X) or CH(—(CH$_2$)$_m$—NXY);
U represents NH, O or CH$_2$;
V represents (CH$_2$)$_a$;
W represents (CH$_2$)$_b$;
a and b independently represent an integer 0 to 3, provided that a+b is in the range 1 to 3;
X and Y independently represents hydrogen, alkyl C1 to 6, or the group —(CH$_2$)$_n$Q or —NXY represents piperidinyl, pyrrolidinyl, morpholinyl or tetrahydroisoquinolinyl;
Q represents biphenyl or phenyl optionally substituted by one or more groups selected from alkyl C1 to 6, alkoxy C1 to 6, perfluoroalkyl C1 to 6, halogen, nitro or cyano;

m represents an integer 0 to 5;

n represents an integer 0 to 6;

or the chain U—V—A—W is as defined above save that it may be unsaturated, or the chain U—V—A—W may represent —NH—CH$_2$—CH$_2$—O— substituted at a carbon atom by the group —(CH$_2$)$_m$—NXY, wherein m, X and Y are as defined above, or a pharmaceutically acceptable salt thereof.

2. A method according to claim 1, in which D represents a five membered heterocyclic ring containing one heteroatom selected from O, N or S, optionally substituted.

3. A method according to claim 1, in which U represents CH$_2$.

4. A method according to claim 1 in which the compound of formula (I) is N-((2-(phenylmethyl)amino)-1,2,3,4-tetrahydronaphth-7-yl)-2-thiophenecarboximidamide or a pharmaceutically acceptable salt thereof.

5. A method according to claim 1 in which the compound of formula (I) is N-((2-amino)-1,2,3,4-tetrahydronaphth-7-yl)-2-thiophenecarboximidamide or a pharmaceutically acceptable salt thereof.

6. A method according to claim 1 in which the compound of formula (I) is N-(1,2,3,4-tetrahydroisoquinoline-7-yl)thiophene-2-carboximidamide or a pharmaceutically acceptable salt thereof.

7. A method according to claim 1 in which the compound of formula (I) is administered in the form of a pharmaceutical composition.

8. A method according to claim 1 in which the disease or condition is stroke.

9. A method according to claim 1 in which the disease or condition is schizophrenia.

10. A method according to claim 1 in which the disease or condition is anxiety.

11. A method according to claim 1 in which the disease or condition is pain.

12. A pharmaceutical composition comprising N-((2-(phenylmethyl)amino)-1,2,3,4-tetrahydronaphth-7-ul)-2-thiophenecarboximidamide or a pharmaceutically acceptable salt thereof in a pharmaceutically acceptable diluent or carrier for oral or parenteral administration.

13. A pharmaceutical composition comprising N-((2-amino)-1,2,3,4-tetrahydronaphth-7-yl)-2-thiophenecarboximidamide or a pharmaceutically acceptable salt thereof in a pharmaceutically acceptable diluent or carrier for oral or parenteral administration.

14. A pharmaceutical composition comprising N-(1,2,3,4-tetrahydroisoquinoline-7-yl)thiophene-2-carboximidamide or a pharmaceutically acceptable salt thereof in a pharmaceutically acceptable diluent or carrier for oral or parenteral administration.

15. A method according to claim 1 in which the disease or condition is Parkinson's disease.

16. A method according to claim 1 in which the disease or condition is migraine or other vascular headache.

* * * * *